US008986742B2

(12) United States Patent
Nakamura et al.

(10) Patent No.: US 8,986,742 B2
(45) Date of Patent: Mar. 24, 2015

(54) RUTILE-TYPE TITANIUM DIOXIDE AND COSMETICS USING THE SAME

(71) Applicant: Titan Kogyo Kabushiki Kaisha, Ube (JP)

(72) Inventors: Akira Nakamura, Yamaguchi (JP); Masayasu Morishita, Yamaguchi (JP); Hisayoshi Funatsu, Yamaguchi (JP); Caihong Liu, Yamaguchi (JP)

(73) Assignee: Titan Kogyo Kabushiki Kaisha, Ube-shi (JP)

( * ) Notice: Subject to any disclaimer, the term of this patent is extended or adjusted under 35 U.S.C. 154(b) by 0 days.

(21) Appl. No.: 14/057,272

(22) Filed: Oct. 18, 2013

(65) Prior Publication Data

US 2014/0112965 A1 Apr. 24, 2014

(30) Foreign Application Priority Data

Oct. 24, 2012 (JP) ................................ 2012-234670

(51) Int. Cl.

*A61Q 17/04* (2006.01)
*A61K 8/02* (2006.01)
*C01G 23/053* (2006.01)
*C09C 1/36* (2006.01)
*B82Y 30/00* (2011.01)

(52) U.S. Cl.

CPC .............. *A61K 8/0275* (2013.01); *A61Q 17/04* (2013.01); *C01G 23/0532* (2013.01); *C09C 1/3661* (2013.01); *C09C 1/3669* (2013.01); *C09C 1/3684* (2013.01); *B82Y 30/00* (2013.01); *Y10S 977/773* (2013.01); *C01P 2004/04* (2013.01); *C01P 2004/16* (2013.01); *C01P 2004/50* (2013.01); *C01P 2004/62* (2013.01); *C01P 2004/64* (2013.01); *C01P 2006/12* (2013.01)

USPC ........... 424/489; 423/610; 424/401; 428/402; 977/773

(58) Field of Classification Search

CPC ....... C01G 23/047; C01G 23/053; A61K 8/29

See application file for complete search history.

(56) References Cited

U.S. PATENT DOCUMENTS

2010/0189666 A1* 7/2010 Nakamura et al. .............. 424/59

FOREIGN PATENT DOCUMENTS

| | | |
|---|---|---|
| EP | 2 216 296 A2 | 8/2010 |
| JP | 9-202722 | 8/1997 |
| JP | 11-322337 | 11/1999 |
| JP | 2010-173863 | 8/2010 |
| WO | WO 2011077084 A1 * | 6/2011 |

OTHER PUBLICATIONS

Extended European Search Report issued Dec. 20, 2013 in Patent Application No. 13189090.7.

* cited by examiner

*Primary Examiner* — Brian Gulledge
*Assistant Examiner* — Isaac Shomer
(74) *Attorney, Agent, or Firm* — Oblon, McClelland, Maier & Neustadt, L.L.P.

(57) ABSTRACT

A Rutile-type titanium dioxide having a rectangular particulate form configured such that major axial planes of rod-shaped particles having a minor axis diameter of 3 to 10 nm are oriented and aggregated in the minor axial direction, and a rod-shaped rutile-type titanium dioxide obtained by treating the rectangular rutile-type titanium dioxide with heat, wherein an apparent average major axial length of the oriented and aggregated particles is 100 to 400 nm, an apparent average minor axial length thereof is 30 to 150 nm, an apparent average axial ratio represented by apparent average major axial length/apparent average minor axial length is 2 to 5 and a specific surface area thereof is 10 to 100 $m^2/g$.

9 Claims, 3 Drawing Sheets

0.1 μm

RUTILE-TYPE TITANIUM DIOXIDE AND COSMETICS USING THE SAME

TECHNICAL FIELD

The present invention relates to rutile-type titanium dioxide configured such that rod-shaped fine particles are oriented and aggregated into rectangular forms, and rod-shaped rutile-type titanium dioxide obtained by treating the rectangular rutile-type titanium dioxide with heat.

Furthermore, the present invention relates to cosmetics containing the rutile-type titanium dioxide and having a UV-shielding function in a wide range from UVB to UVA.

BACKGROUND ART

Recently, UV-rays have been recognized to give harmful influences on the skin and sunscreen cosmetics for preventing UV-rays have been increasingly demanded. In addition, also in makeup cosmetics for helping the skin appear uniform and beautiful, enhancing the UV-shielding effect has been demanded. To satisfy such demands, cosmetics containing a UV-scattering agent such as fine particulate titanium dioxide and fine particulate zinc oxide and an organic UV absorber have been developed; however, these cosmetics are required to be further enhanced in a UV-shielding effect. To enhance a UV-shielding effect, generally, a UV-scattering agent or a UV absorber is added in a large amount. However, if a UV-scattering agent such as fine particulate titanium dioxide is blended in a large amount in a cosmetic, it results in grainy on the skin and a cosmetic forms a thick film to decrease transparency. In addition, a large content of UV absorber has a safety problem. If a person of a sensitive skin uses such a cosmetic, the person may develop a skin trouble such as rash. Actually, the content is limited by regulations, and thus, a large amount of argent cannot be blended. For these reasons, development of a UV-scattering agent, more specifically, titanium dioxide having high UV-shielding performance, in other words, titanium dioxide shielding UV rays in a small content, has been strongly desired.

On the other hand, fine particulate titanium dioxide has a satisfactory shielding effect against the UVB region (280 to 320 nm) and is blended in order to improve SPF (Sun Protection Factor) serving as an index for UVB shielding property; however its effect of shielding UV rays in the UVA region (320 to 400 nm) is insufficient. Therefore, in the country, fine particulate zinc oxide is generally used as a UVA shielding agent. However, in Europe, zinc oxide is not approved as a UV-shielding agent for cosmetics. In addition, if zinc oxide is blended in a large concentration, ions elute and irritate skin. This is a matter of concern. For these reasons, development of titanium dioxide having high UVA shielding effect has been increasingly demanded.

Absorption or scatteration of light by titanium dioxide brings the UV-shielding performance of fine particulate titanium dioxide. The shielding effect against the UVB region is due to absorption of light by a band gap; however, the shielding effect against the UVA region is due to scattering and there is a particle diameter at which maximum shielding performance can be obtained. With respect to the light scattering of titanium dioxide and particle-diameter dependency of UV protection effect, a computational approach based on the Mie theory (P. Stamatakis et al., J. Coatings Tech, 62 (10), 95 (1990)) is made in Japanese Patent Laid-Open No. 9-202722 (Patent Literature 1). According to the results, in the case of light of 300 nm in wavelength, a maximum shield effect is obtained at a particle diameter of 30 to 60 nm; whereas, in the case of light of 350 nm in wavelength, the most suitable effect is obtained at a particle diameter of 80 nm and in the case of light of 400 nm in wavelength, the most suitable effect is obtained at a particles diameter of 120 nm.

In view of this, the present inventors proposed, in Japanese Patent Laid-Open No. 11-322337 (Patent Literature 2), butterfly-shaped rutile-type titanium dioxide formed of aggregated and/or bound needle shaped fine particles, which have an apparent average major axial length (herein, the term "apparent" is used in order to show that the length is a measured value of the aggregated particles; the same shall apply hereinafter) of 0.1 μm (100 nm) or more. The butterfly-shaped titanium dioxide has more excellent UV-shielding performance in the UVA region than a conventional UV-shielding titanium dioxide; however, the performance is not satisfactory. The present inventors further proposed, in Japanese Patent Laid-Open No. 2010-173863 (Patent Literature 3), titanium dioxide having a particulate form configured such that the major axial planes of individual rod-shaped particles (each having a minor axis diameter of 3 to 10 nm) are oriented and aggregated in the minor axial direction. The titanium dioxide is cocoon-shaped rutile-type titanium dioxide, in which an apparent average major axial length of particles oriented and aggregated is 80 to 300 nm; an apparent average minor axial length of particles oriented and aggregated is 30 to 150 nm; an apparent average axial ratio (represented by a value of apparent average major axial length/apparent average minor axial length) is 1.1 to 4; both ends of the major axis of oriented and aggregated particles have a spherical shape or elliptical shape; and a specific surface area is 120-180 $m^2/g$. The cocoon-shaped rutile-type titanium dioxide has more excellent UV-shielding performance in the UVB region than conventional UV-shielding titanium dioxide; however UV-shielding performance in the UVA region was not satisfactory.

CITATION LIST

Patent Literature

[Patent Literature 1] Japanese Patent Laid-Open No. 9-202722

[Patent Literature 2] Japanese Patent Laid-Open No. 11-322337

[Patent Literature 3] Japanese Patent Laid-Open No. 2010-173863

SUMMARY OF INVENTION

Technical Problem

The present invention was made in order to improve UV-shielding performance of a rutile-type titanium dioxide in the UVA region and directed to providing rutile-type titanium dioxide having a UV-shielding effect in a wide range from UVB to UVA and providing cosmetics using the rutile-type titanium dioxide.

Solution to Problem

The present inventors conducted intensive studies with a view to obtaining rutile-type titanium dioxide having shape-anisotropy and having a satisfactory UVA shielding property without deteriorating UVB shielding property. As a result, they found that rutile-type titanium dioxide having a particulate form configured such that rod-shaped particles are oriented and aggregated into rectangular forms, and rod-shaped rutile-type titanium dioxide obtained by treating the rectangular rutile-type titanium dioxide with heat, wherein, when a film is formed from a paste prepared by dispersing such a rutile-type titanium dioxide in dimethicone and its light transmissivity at a wavelength of 550 nm, 360 nm and 280 nm are represented by $T_{553}$, $T_{360}$, and $T_{280}$, respectively, a value of ($T_{550} \times T_{280}/T_{363}$) of 5.0 to 55.0 is satisfied, are excellent in UV-shielding performance, particularly in UVA shielding property. Based on the finding, the present invention was accomplished.

More specifically, the rutile-type titanium dioxide of the present invention refers to a rutile-type titanium dioxide having a rectangular particulate form configured such that the major axial planes of rod-shaped particles each having a major axis diameter of 30 to 200 nm and a minor axis diameter of 3 to 10 nm, are oriented and aggregated in the minor axial direction, and refers to rod-shaped rutile-type titanium dioxide which is obtained by treating the rectangular rutile-type titanium dioxide with heat. The rutile-type titanium dioxide is characterized in that the oriented and aggregated particles have an apparent average major axial length of 100 to 400 nm, an apparent average minor axial length of 30 to 150 nm, an apparent average axial ratio (represented by apparent average major axial length/apparent average minor axial length) of 2 to 5 and a specific surface area of 10 to 100 $m^2/g$.

The rectangular rutile-type titanium dioxide of the present invention has the same apparent average major axial length, apparent minor axial length and average axial ratio as those of the cocoon-shaped rutile-type titanium dioxide defined in Japanese Patent Laid-Open No. 2010-173863 (Patent Literature 3). The cocoon-shaped rutile-type titanium dioxide of Patent Literature 3 is aggregates of particles which are mutually connected via van der Waals force. In order to form a cocoon shape, the cohesive force between rod-shaped particles is controlled to the extent that projections and depressions are formed on the surface of the aggregates. Voids formed between particles at this time are used for improving UVB shielding property. In contrast, the rectangular rutile-type titanium dioxide of the present invention is obtained by binding particles via van der Waals force similarly to cocoon-shaped particles; however, the cohesive force between mutual rod-shaped particles is strong compared to cocoon-shaped particles, with the result that the surface of aggregated particles is compressed to form a rectangular shape. Furthermore, since high aggregation force is applied, the number of voids within rectangular particles decreases, with the result that aggregated particles behave as an aggregate like a single particle. Therefore, UVA shielding property improves. The cocoon-shaped rutile-type titanium dioxide of Patent Literature 3 is synthesized by adding an aliphatic hydroxy acid compound to an acid-soluble titanium compound under the acidic conditions of hydrochloric acid and performing thermal hydrolysis without performing a deflocculation treatment. In contrast, in the present invention, the pH of an acid-soluble titanium compound is controlled with hydrochloric acid and a deflocculation treatment is performed at a low temperature. Thereafter, hydrochloric acid is further added to the mixture and thermal hydrolysis is performed. In the present invention, a rod-shaped particle serving as a growth nucleus is generated at a low temperature and thereafter thermal hydrolysis is performed in a short time. In this manner, a strong aggregation state can be obtained. Owing to a difference in these cohesive forces for forming particles, the specific surface area of the cocoon-shaped rutile-type titanium dioxide of Patent Literature 3 is 120 to 180 $m^2/g$; whereas, the specific surface area of the rutile-type titanium dioxide of the present invention is as small as 10 to 100 $m^2/g$.

The rectangular rutile-type titanium dioxide of the present invention is obtained by controlling the pH of a solution containing an acid-soluble titanium compound to 1 to 3 with hydrochloric acid, performing a deflocculation treatment at a temperature of 10 to 30° C., and further adding hydrochloric acid to perform hydrolysis at a temperature of 20 to 80° C. Furthermore, the obtained rectangular rutile-type titanium dioxide is treated with heat to obtain rod-shaped rutile-type titanium dioxide.

Furthermore, the particle surface of the rutile-type titanium dioxide can be coated with a layer of an inorganic substance and/or an organic substance. The inorganic substance is preferably a water-containing oxide or an oxide of one or more of compounds selected from aluminum, silicon, zinc, titanium, zirconium, iron, cerium and tin.

Furthermore, the organic substance is preferably one or more of compounds selected from a silicone compound, a coupling agent, a fluorine compound and a fatty acid. Furthermore, cosmetics can be obtained using the rutile-type titanium dioxide.

Advantageous Effects of Invention

In the rutile-type titanium dioxide of the present invention having a rectangular particulate form configured such that rod-shaped particles are oriented and aggregated into rectangular forms and the rod-shaped rutile-type titanium dioxide prepared by treating the rectangular rutile-type titanium dioxide with heat into a rod-shape, an apparent major axial length of particles oriented and aggregated is 100 nm to 400 nm, an apparent average minor axial length thereof is 30 to 150 nm and an apparent average axial ratio (represented by an apparent average major axial length/apparent average minor axial length) is 2 to 5 and a specific surface area is 10 to 100 $m^2/g$. When the rutile-type titanium dioxide of the present invention having such features is dispersed in dimethicone to prepare paste and a coating film of the paste is formed, assuming that its light transmissivity at a wavelength 550 nm, 360 nm and 280 nm are represented by $T_{550}$, $T_{360}$, and $T_{280}$, respectively, a value of ($T_{550} \times T_{280}/T_{360}$) becomes 5.0 to 55.0. Thus, the rutile-type titanium dioxide of the present invention has excellent UV-shielding performance compared to a conventional rutile-type titanium dioxide, in particular, excellent UVA shielding property, and can provide cosmetics having more excellent UV-shielding performance than cosmetics using conventional titanium dioxide. Herein, $T_{550}$ represents a transmissivity of visible light in the center wavelength range. If this value is large, transparency is high by itself. Furthermore, as already described, $T_{280}$ represents a transmissivity in the UVB wavelength region; whereas $T_{360}$ represents a transmissivity in the UVA wavelength region. Since a value of ($T_{550} \times T_{280}/T_{360}$) is represented by a product of $T_{550}$, the higher the visible light transmissivity, the higher the value. Furthermore, this value is in proportional to a reciprocal number of $T_{360}$. Therefore, the more excellent the shielding performance in the UVA region, the higher the value. In contrast, if shielding performance in the UVB region is high, this value is low by itself. The value, if it is excessively low, means that transparency is low or the UV-shielding performance in the UVA region is low compared to UV-shielding performance in the UVB region. Because of this, an excessive low value is not preferable. Conversely, an excessively high value suggests that the UV-shielding performance in the UVB region is low compared to UV-shielding performance in the UVA region.

DESCRIPTION OF EMBODIMENTS

Figures 1, 2:
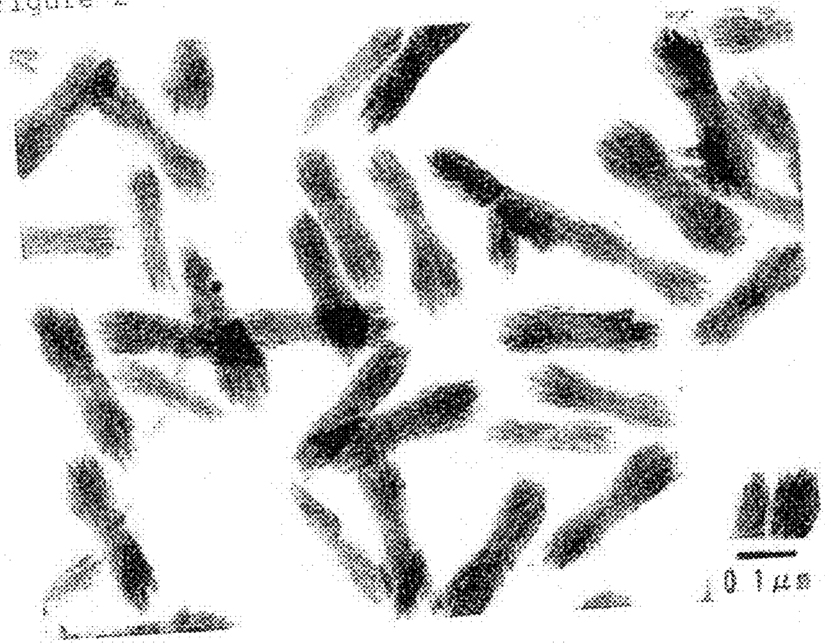
FIG. 1 shows a micrograph of rectangular rutile-type titanium dioxide obtained in Example 1, observed under a transmission electron microscope.
FIG. 2 shows a micrograph of rectangular rutile-type titanium dioxide obtained in Example 2, observed under a transmission electron microscope.

Now, the rutile-type titanium dioxide of the present invention will be more specifically described. The rutile-type titanium dioxide of the present invention refers to rectangular aggregated rutile-type titanium dioxide particles constituted of particles oriented in the form of a bundle or rod-shaped rutile-type titanium dioxide obtained by treating the rectangular rutile-type titanium dioxide with heat into a rod-shape. As already described, the rectangular or rod-shaped rutile-type titanium dioxide is characterized in that the particles oriented and aggregated have an apparent average major axial length of 100 to 400 nm, an apparent average minor axial length of 30 to 150 nm, an apparent average axial ratio (represented by apparent average major axial length/apparent average minor axial length) of 2 to 5 and a specific surface area of 10 to 100 $m^2/g$. Individual particles constituting aggregated particles of the rectangular rutile-type titanium dioxide of the present invention have a rod-shape. Whereas the spindle-shaped particles known in the art have a smooth surface, the rectangular particles, each are an aggregate obtained by binding particles via van der Waals force, have small projections and depressions in the surface. By the presence of the projections and depressions, the absorption/scattering rate of UV light increases to improve UV-shielding performance. Furthermore, in the rectangular particles obtained by treating the rod-shaped particles with heat, each of the rod-shaped fine particles constituting a rectangular shape grows by heat treatment and crystallinity thereof increases, with the result that UV-shielding performance is further improved. Furthermore, whereas the spindle-shaped particles have a cylindrical shape with a thick center and tapered ends in the major axis, the rectangular or rod-shaped particles of the present invention have slightly widened ends in the major axis since the particles are constituted of fine rod-shaped particles.

(Production Method)

A method for producing the rutile-type titanium dioxide of the present invention will be more specifically described. The rectangular rutile-type titanium dioxide of the present invention is obtained by adding hydrochloric acid to an acid-soluble titanium compound to control pH to 1 to 3, performing a deflocculation treatment at a temperature of 10 to 30° C., further adding hydrochloric acid, and performing thermal hydrolysis. The conditions of hydrolysis needs to be appropriately controlled depending upon the acid solubility of a starting acid-soluble titanium compound. For example, if ortho-titanic acid, which is obtained by neutralizing a titanyl sulfate solution or a titanium tetrachloride solution with an alkali, is used as an acid-soluble titanium compound, the rutile-type titanium dioxide of the present invention is obtained by adding hydrochloric acid to the ortho-titanic acid to control pH to 1 to 3, performing deflocculation at a temperature of 10 to 30° C., further adding hydrochloric acid to control the concentration of $TiO_2$ to be 50 to 140 g/L and preferably 60 to 120 g/L, and the concentration of hydrochloric acid to be 60 to 120 g/L and preferably 70 to 100 g/L, and performing hydrolysis at 20 to 80° C. and preferably 25 to 60° C. If an unreacted titanium compound remains, aging is preferably performed at a temperature of 95° C. or more for 2 to 8 hours after the hydrolysis in order to complete the reaction. Since aggregation of rectangular particles is destroyed if they are allowed to age for a long time, reducing dispersibility, the aging time is appropriately set within 8 hours.

The type of acid-soluble titanium compound used in the present invention is not limited as long as it is a titanium compound soluble in hydrochloric acid and ortho-titanic acid, which is Obtained by neutralizing titanyl sulfate or titanium tetrachloride with an alkali at a low temperature, is preferable. Alternatively, an alkali salt of titanic acid obtained by an alkali treatment of a meta-titanic acid can be used.

Furthermore, the obtained rectangular rutile-type titanium dioxide is treated with heat to obtain rod-shaped rutile-type titanium dioxide. The temperature of the heat treatment varies depending upon the size of aggregated particles of the rectangular rutile titanium dioxide; however, the temperature is preferably 300 to 700° C. If the temperature is lower than 300° C., crystallization does not proceed. In contrast, if the temperature is higher than 700° C., sintering proceeds, with the result that transparency of cosmetics employing the particles decreases.

(Surface Coating Layer)

To improve dispersion stability and durability in a dispersion medium in producing a cosmetic, the surface of the aggregated particles can be coated with an inorganic substance. Examples of the inorganic substance that can be used include water-containing oxides or oxides of metals such as aluminum, silicon, zinc, titanium, zirconium, iron, cerium and tin. The type of metal salt to be used for coating is not particularly limited. Furthermore, before blending each of these titanium dioxides in a cosmetic, water repellent treatment and/or oil repellent treatment can be applied in advance. In these treatments, organic substances are used. Examples of the organic substances include silicone compounds such as dimethylpolysiloxane and methyl hydrogen polysiloxane; coupling agents such as a silane coupling agent, an aluminum coupling agent, a titanium coupling agent and a zirconium coupling agent; fluorine compounds such as a perfluoroalkyl phosphate compound; hydrocarbons, lecithin, amino acids, polyethylene, wax, and fatty acids such as lauric acid and stearic acid.

(Inorganic Pigment and Organic Pigment that can be Used in Combination)

In obtaining a cosmetic containing the rutile-type titanium dioxide of the present invention as a component, various types of components such as an inorganic pigment and an organic pigment that are generally used in cosmetics, can be used, if necessary, in combination, in the cosmetic of the present invention. Examples of the inorganic pigment that can be used in combination include titanium dioxide, zinc oxide, red iron oxide, yellow iron oxide, black iron oxide, ultramarine blue pigment, iron blue pigment, cerium oxide, talc, white mica, synthetic mica, brown mica, black mica, synthesized fluorinated brown mica, mica titanium, micaceous iron oxide, sericite, zeolite, kaolin, bentonite, clay, silicic acid, silicic anhydride, magnesium silicate, aluminum silicate, calcium silicate, barium sulfate, magnesium sulfate, calcium sulfate, calcium carbonate, magnesium carbonate, boron nitride, bismuth oxychloride, alumina, zirconium oxide, magnesium oxide, chromium oxide, calamine, hydroxyapatite and a complex of these. Examples of the organic pigment that can be used in combination include a silicone powder, an elastic silicone powder, a polyurethane powder, a cellulose powder, a nylon powder, a urethane powder, a silk powder, poly methyl methacrylate (PMMA) powder, starch, a polyethylene powder, a polystyrene powder, carbon black, tar dye, a natural dye, a metal soap such as zinc stearate and a complex thereof.

(Components that can be Blended)

In addition, in the cosmetic of the present invention, components other than the aforementioned components may be blended in accordance with an object as long as the components do not quantitatively or qualitatively damage the effects of the invention. For example, an oily ingredient, a dye, a pH moderator, a moisturizer, a thickener, a surfactant, a dispersing agent, a stabilizer, a coloring agent, a preservative, an antioxidant, a sequestering agent, an astringent, an anti-inflammatory agent, a UV absorber and a fragrance can be appropriately blended as long as an object of the invention can be attained.

(Form of Cosmetic)

The cosmetics of the present invention can be produced by a method known in the art. As a form of the cosmetic, any type of form such as a powder, a solid powder, a cream, a milk liquid, lotion, an oily liquid, a solid oil and a paste may be taken. The cosmetics of the present invention may be, for example, a makeup base, a foundation, a concealer, a face powder, a control color, a sun-screen cosmetic, a lipstick, a lip cream, an eye shadow, an eyeliner, a mascaras, a brusher, a manicure, a body powder, a perfume powder and a baby powder; skin care cosmetics or hair care cosmetics.

(Contents of Rectangular and Rod-Shaped Rutile-Type Titanium Dioxide)

The total content of the rectangular and/or rod-shaped rutile-type titanium dioxide of the present invention in these cosmetics, which can be arbitrarily set depending upon the properties of cosmetics to be required, is 0.1 to 50 wt %, and preferably 1 to 45 wt %. To the rectangular and/or rod-shaped rutile-type titanium dioxide of the present invention, titanium dioxide having a different particle diameter or a different shape may be blended depending upon the purpose.

EXAMPLES

Now, the present invention will be more specifically described by way of Examples, below. The following Examples are shown just as illustrations, which will not be construed as limiting the scope of the invention.

Example 1

Synthesis of Rutile-Type Titanium Dioxide

In a 160 g/L sodium carbonate solution, a solution containing titanyl sulfate (100 g/L) as $TiO_2$ was slowly added dropwise such that the liquid temperature did not exceed 25° C. Addition was terminated when pH reached 10. The white precipitate of ortho-titanic acid obtained by the neutralization, was filtered and sufficiently washed. After the ortho-titanic acid cake washed was repulped by use of diluted hydrochloric acid (200 g/L), the pH thereof was controlled to 2 with the same diluted hydrochloric acid and deflocculation was performed at 10° C. for 3 hours. Subsequently, a 400 g/L concentrated hydrochloric acid was added such that the liquid temperature did not exceed 30° C. to control a $TiO_2$ concentration to 100 g/L and a hydrochloric acid concentration to 80 g/L. Next, the solution was warmed while stirring to adjust the liquid temperature to 30° C. and hydrolysis was performed for one hour. Thereafter, aging was further performed at 95° C. for 3 hours to synthesize rutile-type titanium dioxide. When the shape and particle diameter of the rutile-type titanium dioxide obtained were observed by a transmission electron microscope, rectangular aggregated particles formed of rod-shaped particles aggregated and oriented in the form of a bundle were observed, which had an apparent average major axial length of 250 nm, an apparent average minor axial length of 60 nm, an apparent average axial ratio of 4.2 and a specific surface area of 75 $m^2/g$. A micrograph of the particles observed by a transmission electron microscope is shown in FIG. 1.

Surface Treatment:

An aqueous suspension solution containing the obtained rutile-type titanium dioxide was warmed and controlled to have a temperature of 70° C. Subsequently, 10 wt % sodium aluminate in terms of $Al_2O_3$ to titanium dioxide was slowly added while stirring. After the mixture was stirred for one hour, a 100 g/L diluted sulfuric acid was added to control pH to 8.0. Next, a 5 wt % sodium stearate to titanium dioxide was added. After the mixture was stirred for one hour, pH was controlled to 6.5 by diluted sulfuric acid. After filtration and washing with water, the resultant titanium dioxide was dried by a dryer at 110° C. for 12 hours to obtain surface-treated rutile-type titanium dioxide.

Example 2

Synthesis of Rutile-Type Titanium Dioxide

The white precipitate of ortho-titanic acid obtained in the same manner as in Example 1 was filtered and sufficiently washed. After the ortho-titanic acid cake washed was repulped with diluted hydrochloric acid (200 g/L), the pH was controlled with the same diluted hydrochloric acid to 1 and deflocculation was performed at 10° C. for 3 hours. Subsequently, concentrated hydrochloric acid (400 g/L) was added such that the liquid temperature did not exceed 30° C. to control a $TiO_2$ concentration to 80 g/L and a hydrochloric acid concentration to 110 g/L. Next, the solution was warmed while stirring to adjust liquid temperature to 45° C. and hydrolysis was performed for 3 hours. Thereafter, aging was further performed at 95° C. for 3 hours to synthesize rutile-type titanium dioxide. When the shape and particle diameter of the obtained rutile-type titanium dioxide was observed by a transmission electron microscope, the particles were rectangular particles formed of rod-shaped particles aggregated and oriented in the form of bundle having an apparent average major axial length of 300 nm, an apparent average minor axial length of 80 nm, an apparent average axial ratio of 3.8 and a specific surface area of 88 $m^2/g$. A micrograph of the particles observed by a transmission electron microscope is shown in FIG. 2.

Surface Treatment:

Surface-treated rutile-type titanium dioxide was obtained in the same manner as in Example 1.

Example 3

Figure 3:
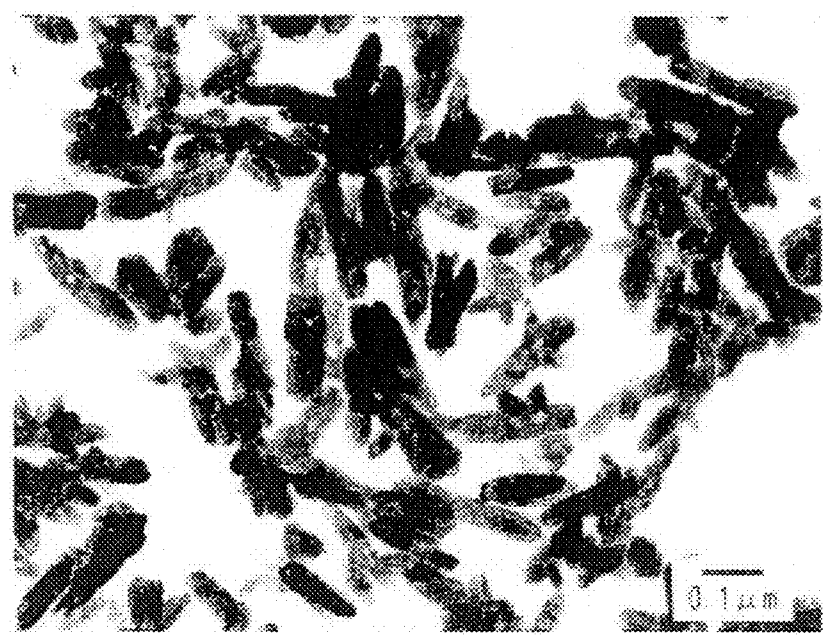
FIG. 3 shows a micrograph of rod-shaped rutile-type titanium dioxide obtained in Example 3, observed under a transmission electron microscope.

To the aqueous suspension solution containing the rutile-type titanium dioxide obtained in Example 1, a sodium hydroxide solution (400 g/L) was added while stirring to control (neutralize) the suspension solution to pH 6.0. After filtration and washing with water, dehydration was performed by a dryer at 110° C. for 12 hours. The resultant dried powder sample was pyrolyzed in air at 550° C. for one hour. The shape of the resultant rutile-type titanium dioxide was observed by a transmission electron microscope and shown in FIG. 3. The particles were rod-shaped oriented/aggregated particles having an apparent average major axial length of 170 nm, an apparent average minor axial length of 40 nm, an apparent average axial ratio of 4.3 and a specific surface area of 27 $m^2/g$.

Surface Treatment:

The obtained rutile-type titanium dioxide was repulped and warmed to control the temperature to 70° C. Subsequently, 2 wt % sodium aluminate in terms of $Al_2O_3$ to titanium dioxide was slowly added while stirring. After the mixture was stirred for one hour, a 100 g/L diluted sulfuric acid was added to control pH to 8.0. Next, a 2 wt % sodium stearate to titanium dioxide was added. After the mixture was stirred for one hour and pH was controlled to 6.5 by diluted sulfuric acid. After filtration and washing with water, dehydration was performed by a dryer at 110° C. for 12 hours to obtain surface-treated rutile-type titanium dioxide.

Comparative Example 1

Synthesis of Rutile-Type Titanium Dioxide

Figure 4:
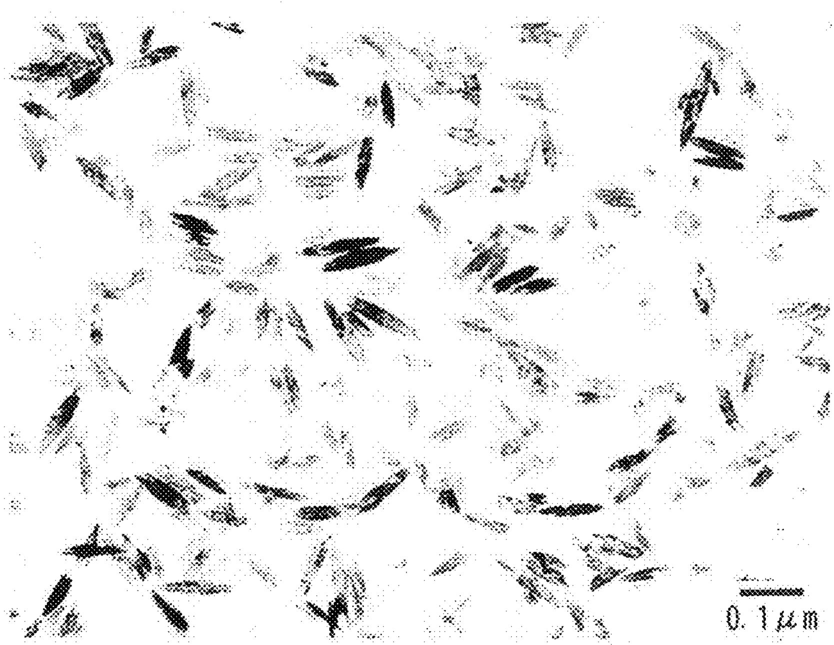
FIG. 4 shows a micrograph of spindle-shaped rutile-type titanium dioxide obtained in Comparative Example 1, observed under a transmission electron microscope.

A titanyl sulfate solution was pyrolyzed, filtered and washed to obtain water-containing titanium dioxide slurry. To the slurry, a 400 g/L sodium hydroxide solution was added while stirring such that the weight ratio of NaOH to $TiO_2$ is 3 and the mixture was heated at 95° C. for 2 hours. Subsequently, the treated product was sufficiently washed. To the resultant slurry, hydrochloric acid (400 g/L) was added while stirring to control a $TiO_2$ concentration to 90 g/L, a hydrochloric acid concentration to 80 g/L. Hydrolysis was performed at 95° C. for 2 hours to synthesize rutile-type titanium dioxide. When the shape and particle diameter of the obtained rutile-type titanium dioxide was observed by a transmission electron microscope, the particles were spindle-shaped particles not aggregated having an average major axial length of 80 nm, an average minor axial length of 10 nm and a specific surface area of 98 $m^2/g$, as shown in FIG. 4.

Surface Treatment:

Surface-treated rutile-type titanium dioxide was obtained by performing a surface treatment in the same manner as in Example 1.

Comparative Example 2

Synthesis of Rutile-Type Titanium Dioxide

Figure 5:
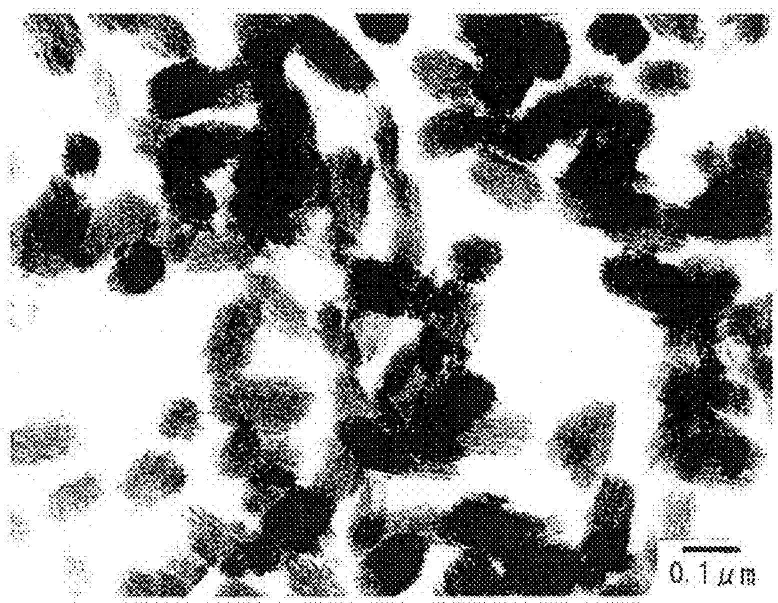
FIG. 5 shows a micrograph of cocoon-shaped rutile-type titanium dioxide obtained in Comparative Example 2, observed under a transmission electron microscope.
Figure 6:
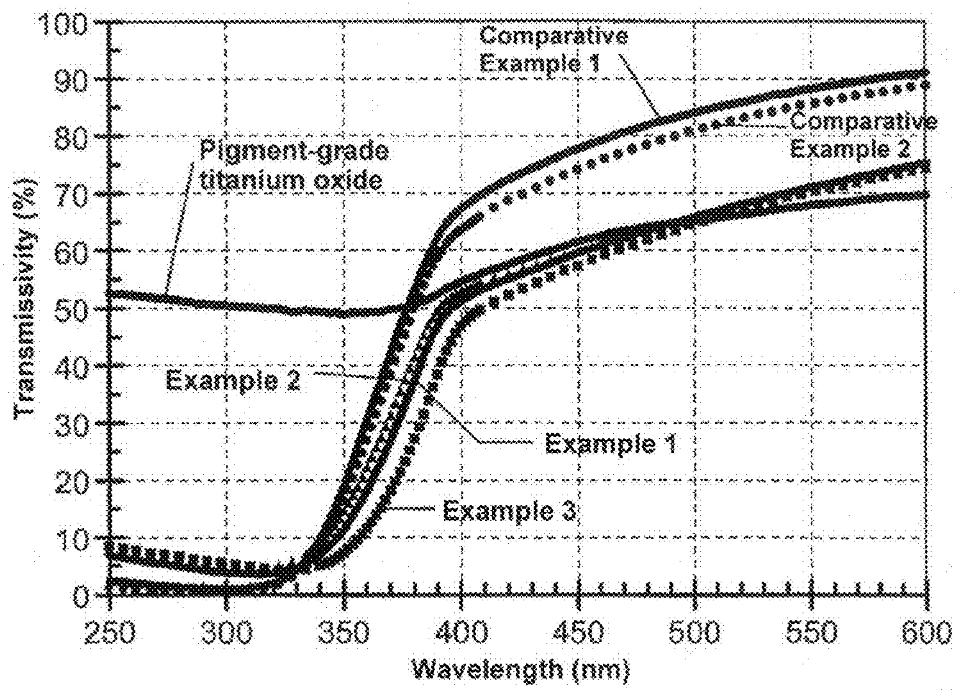
FIG. 6 is an absorbance curve of rutile-type titanium dioxides obtained in Examples 1 to 3 and Comparative Examples 1 and 2.

The white precipitate of ortho-titanic acid obtained in the same manner as in Example 1 was filtered and sufficiently washed. After the ortho-titanic acid cake washed was repulped with diluted hydrochloric acid (200 g/L), deflocculation was skipped and concentrated hydrochloric acid (400 g/L) and citric acid powder were added to control a $TiO_2$ concentration to 80 g/L, a hydrochloric acid concentration to 110 g/L and a citric acid concentration to 4.0 g/L. Subsequently, the solution was warmed while stirring to adjust liquid temperature to 45° C. and hydrolyzed for 20 hours while stirring to synthesize rutile-type titanium dioxide. The resultant rutile-type titanium dioxide was observed by a transmission electron microscope and the results are shown in FIG. 5. The particles were cylindrical cocoon-shaped particles in which rod-shaped particles are oriented in the form of a bundle and aggregated, having an average major axial length of 105 nm, an average minor axial length of 70 nm, an average axial ratio of 1.5 and a specific surface area of 148 $m^2/g$.

Surface Treatment:

Surface-treated rutile-type titanium dioxide was obtained by performing a surface treatment in the same manner as in Example 1.

For reference, average major axial lengths, average minor axial lengths, average axial ratios and specific surface areas of the particles of Examples 1 to 3 and Comparative Examples 1 to 2 are shown below.

TABLE 1

| Sample name | Major axial length (nm) | Minor axial length (nm) | Axial ratio | Specific surface area ($m^2/g$) |
|---|---|---|---|---|
| Example 1 | 250 | 60 | 4.2 | 75 |
| Example 2 | 300 | 80 | 3.8 | 88 |
| Example 3 | 170 | 40 | 4.3 | 27 |
| Comparative Example 1 | 80 | 10 | 8.0 | 98 |
| Comparative Example 2 | 105 | 70 | 1.5 | 148 |

(Evaluation of UV-Shielding Performance)

From each of the rutile-type titanium dioxides obtained in Examples 1 to 3, the spindle-shaped rutile-type titanium dioxide obtained in Comparative Example 1 and the cocoon-shaped rutile-type titanium dioxide obtained in Comparative Example 2 and pigment-glade rutile-type titanium dioxide (CR-50 manufactured by Ishihara Sangyo Kaisha, Ltd.) having an average particle diameter of 250 nm, a sample (0.05 g) was taken and kneaded together with dimethylpolysiloxane (1.95 g, 5000 cs) by use of Hoover's muller under load of 150 Lbs. for 50 revolutions. Each of the obtained paste was applied to a quartz glass plate by use of a film applicator with a film thickness of 23 μm and transmissivity was measured by use of a V-670 type spectrophotometer (manufactured by JASCO Corporation). The results are shown in Table 2 and FIG. 1. Herein, the light transmissivity values at wavelengths of 550 nm, 360 nm and 280 nm are represented as $T_{550}$, $T_{360}$ and $T_{280}$, respectively.

TABLE 2

| | Transmissivity (%) | | | |
|---|---|---|---|---|
| Sample name | $T_{550}$ (550 nm) | $T_{360}$ (360 nm) | $T_{280}$ (280 nm) | $T_{550} \times T_{280}/T_{360}$ |
| Example 1 | 71.0 | 18.2 | 4.9 | 19.3 |
| Example 2 | 70.1 | 22.3 | 5.8 | 18.2 |
| Example 3 | 70.4 | 11.5 | 6.6 | 40.3 |
| Comparative Example 1 | 88.1 | 30.5 | 1.3 | 3.72 |
| Comparative | 85.5 | 26.9 | 0.6 | 1.86 |

TABLE 2-continued

| Sample name | Transmissivity (%) | | | |
|---|---|---|---|---|
| | $T_{550}$ (550 nm) | $T_{360}$ (360 nm) | $T_{280}$ (280 nm) | $T_{550} \times T_{280}/T_{360}$ |
| Example 2 Pigment-grade titanium dioxide | 67.8 | 49.2 | 51.3 | 70.7 |

As is apparent form Table 2 and FIG. 1, the rutile-type titanium dioxides obtained in Examples 1 to 3 have high UV-shielding performance, compared to the rutile-type titanium dioxides obtained in Comparative Examples 1 to 2 and the pigment-grade titanium dioxide, in particular, the effect is clearly exerted in the UVA region.

(Cosmetics)

Now, cosmetics containing the rectangular titanium dioxide powder of the present invention will be described below.

Formulation Example 1

W/O Emulsion Type Foundation

The rutile-type titanium dioxides obtained in Examples 1 to 3, the spindle-shaped rutile-type titanium dioxide obtained in Comparative Example 1, the cocoon-shaped rutile-type titanium dioxide obtained in Comparative Example 2, and further the aforementioned commercially available pigment-grade titanium dioxide were used to prepare W/O emulsion type foundations.

| (Component) | Weight (%) |
|---|---|
| 1. POE modified silicone (HLB = 4.5) | 0.8 |
| 2. Polyglyceryl-polyricinoleate | 0.5 |
| 3. Neopentyl glycol dicaprate | 3.0 |
| 4. Squalane | 1.0 |
| 5. Pentaerythrityl tetraoctanoate | 2.0 |
| 6. Stearoyl Inulin (Note 1) | 1.0 |
| 7. Cyclomethicone | 9.4 |
| 8. Preservative | appropriate amount |
| 9. Antioxidant | appropriate amount |
| 10. Fragrance | appropriate amount |
| 11. Titanium dioxide powder of each of Examples or Comparative Example treated with silicone | 10.0 |
| 12. Silicone treated talc | 4.0 |
| 13. Silicone treated colorant | 1.0 |
| 14. Purified water | Balance |
| 15. 1,3-Butylene glycol | 5.0 |
| 16. Glycerin | 1.0 |
| 17. Sodium chloride | 1.0 |
| 18. Preservatives | appropriate amount |

(Note 1) Rheopearl ISK (manufactured by Chiba Flour Milling Co., Ltd.)

(Production Method)

A: Components 11 to 13 are stirred and blended by a Henschel mixer.

B: The mixture A was added to components 1 to 10 and homogeneously dispersed by a stirrer.

C: In another container, components 14 to 18 are dissolved by heating.

D: The mixture C is added to the mixture B, emulsified and thereafter gradually cooled to room temperature. In this manner, W/O emulsion type foundations were obtained.

(Evaluation of UV-Shielding Performance)

The SPF (Sun Protection Factor) and UVA ratio (a total absorption amount at a wavelength of 320 to 400 nm/a total absorption amount at a wavelength of 290 to 320 nm) of each of the W/O emulsion type foundations prepared were measured by a UV-1000S SPF analyzer manufactured by Labsphere Inc. The results are shown in Table 3.

TABLE 3

| Sample name | SPF | UVA ratio |
|---|---|---|
| Example 1 | 14 | 0.7 |
| Example 2 | 9 | 0.7 |
| Example 3 | 17 | 0.8 |
| Comparative Example 1 | 17 | 0.5 |
| Comparative Example 2 | 22 | 0.5 |
| Pigment-grade titanium dioxide | 3 | 1.0 |

As shown in Table 3, the rutile-type titanium dioxide of the present invention had not only a high UVB shielding performance represented by SPF but also a high UVA shielding performance represented by UVA ratio.

The W/O emulsion type foundations obtained were evaluated for spreadability, smoothness, coverage, powdery finish and makeup-lasting property by sensory tests. The results are shown in Table 4.

TABLE 4

| Measurement sample | Spread-ability | Smooth-ness | Coverage | Powdery finish | Makeup-lasting property |
|---|---|---|---|---|---|
| Example 1 | ◎ | ◎ | ○ | ○ | ◎ |
| Example 2 | ○ | ◎ | ○ | ○ | ◎ |
| Example 3 | ○ | ○ | ◎ | ○ | ○ |
| Comparative Example 1 | Δ | Δ | X | ◎ | Δ |
| Comparative Example 2 | Δ | X | Δ | ○ | ○ |
| Pigment-grade titanium dioxide | Δ | X | ◎ | X | Δ |

Evaluation and Evaluation Criteria

Ten panelists used the W/O emulsion type foundations prepared using any one of titanium dioxides of Examples 1 to 3 and Comparative Examples 1 and 2 and commercially available pigment-grade titanium dioxide, and made sensory evaluation on sensory test items shown in Table 4 based on five-grade criteria. Determination was made based on average scores.

Evaluation Criteria

Extremely satisfactory: 5 points, satisfactory: 4 points, good: 3 points, slightly unsatisfactory: 2 points, unsatisfactory: 1 point Determination Criteria 4.0 to 5.0 points: ◎, 3.0 to less than 4.0 points: ○, 2.0 to less than 3.0 points: Δ, 1.0 to less than 2.0 points: X As the results of the sensory test, any one of the foundations obtained by Examples 1 to 3 of the present invention was excellent in spreadability and smoothness during application, free of powdery finish due to appropriate coverage and provided a natural finish without concealing skin's natural beauty, compared to those of Comparative Examples 1 and 2 and the commercially available pigment-grade titanium dioxide. In addition, the foundations satisfactorily prolonged the wear of makeup and excellently maintained sheer coverage. As described, owing to the content of the rectangular and/or rod-shaped rutile-type titanium dioxide of the present invention in a cosmetic made it possible to provide a cosmetic having excellent UVB and UVA shielding performances and excellent spreadability and smoothness during application without a powdery finish due to appropriate coverage and provide natural finish without concealing skin's natural beauty.

Formulation Example 2

W/O Emulsion Type Sunscreen

W/O emulsion type sunscreens were prepared using the rutile-type titanium dioxides obtained in Examples 1 to 3.

| (Component) | Weight (%) |
|---|---|
| 1. Crosslinked polyether-modified silicone (Note 1) | 2.0 |
| 2. Crosslinked dimethylpolysiloxane (Note 2) | 3.0 |
| 3. Decamethylcyclopentasiloxane | 13.5 |
| 4. Dimethylpolysiloxane (6 $mm^2$/second (25° C.)) | 7.0 |
| 5. Dispersant containing surface-treated titanium dioxide any one of Examples 1 to 3 | 25.0 |
| 6. Silicone treated talc | 4.0 |
| 7. 1,3-Butylene glycol | 5.0 |
| 8. Sodium citrate | 0.4 |
| 9. Sodium chloride | 0.5 |
| 10. Preservative | appropriate amount |
| 11. Purified water | balance |

(Note 1) KSG-210 manufactured by Shin-Etsu Chemical Co., Ltd.
(Note 2) KSG-15 manufactured by Shin-Etsu Chemical Co., Ltd.

(Production Method)

A: Components 1 to 5 are homogeneously mixed and then component 6 is homogeneously dispersed.

B: Components 7 to 11 are homogeneously mixed.

C: The mixture B is gradually added to the mixture A while stirring and emulsified. In this manner, W/O emulsion type sunscreens were obtained.

It was confirmed that the obtained sunscreens can be applied uniformly and lightly spread with excellent adhesiveness and satisfactory adaptability without squeaky feeling and give a fresh sense of use without stickiness or greasiness; at the same time, the sunscreens have satisfactory waterproofness, water repellency, perspiration fastness, excellent makeup-lasting property and stability without a change due to temperature and time.

Formulation Example 3

W/O Cream

W/O creams were prepared using the rutile-type titanium dioxides obtained in Examples 1 to 3.

| (Component) | Weight (%) |
|---|---|
| 1. Crosslinked polyether-modified silicone (Note 1) | 3.5 |
| 2. Crosslinked dimethylpolysiloxane (Note 2) | 5.0 |
| 3. Branched polyether-modified silicone (Note 3) | 1.0 |
| 4. Organic modified bentonite | 1.2 |
| 5. Triethylhexanoin | 5.0 |
| 6. Dimethylpolysiloxane (6 $mm^2$/second (25° C.)) | 5.5 |
| 7. Decamethylcyclopentasiloxane | 9.0 |
| 8. Acrylic silicone resin dissolved product (Note 4) | 1.5 |
| 9. Dispersant containing surface-treated titanium dioxide any one of Examples 1 to 3 | 25.0 |
| 10. 1,3-Butylene glycol | 5.0 |
| 11. Sodium citrate | 0.4 |
| 12. Purified water | balance |

(Note 1) KSG-210 manufactured by Shin-Etsu Chemical Co., Ltd.
(Note 2) KSG-15 manufactured by Shin-Etsu Chemical Co., Ltd.
(Note 3) KF-6028 manufactured by Shin-Etsu Chemical Co., Ltd.
(Note 4) KP-575 manufactured by Shin-Etsu Chemical Co., Ltd.

(Production Method)

A: Components 1 to 8 are mixed and homogeneously dispersed.

B: Component 10, 11 and 12 are mixed and dissolved.

C: The mixture B is added to the mixture A and homogeneously mixed.

D: Component 9 is added to the mixture C and homogeneously mixed. In this manner, W/O creams were obtained.

It was confirmed that the obtained W/O creams are lightly spread without squeaky feeling, have satisfactory adaptability with excellent adhesiveness, provide a moist, watery and fresh sense of use and pleasant cooling sensation; at the same time, W/O creams have satisfactory makeup lasting property and extremely excellent usability and stability without a change due to temperature and time.

Formulation Example 4

Powdery Foundation

Powdery foundations were prepared using the rutile-type titanium dioxides obtained in Examples 1 to 3.

| (Component) | Weight (%) |
|---|---|
| 1. Caprylylsilane-treated mica (Note 1) | 40.0 |
| 2. Powder according to any one of Examples 1 to 3 | 5.0 |
| 3. Silicone-treated talc (Note 2) | balance |
| 4. Silicone-treated pigment-grade titanium dioxide (Note 2) | 5.0 |
| 5. Silicone-treated fine particulate titanium dioxide (Note 2) | 5.0 |
| 6. Silicone-treated barium sulfate (Note 2) | 10.0 |
| 7. Silicone-treated iron red (Note 2) | 0.4 |
| 8. Silicone-treated yellow iron oxide (Note 2) | 2.0 |
| 9. Silicone-treated amber (Note 2) | 0.4 |
| 10. Silicone-treated black iron oxide (Note 2) | 0.1 |
| 11. Phenyl-modified hybrid silicone composite powder (Note 3) | 2.0 |
| 12. Spherical polymethyl silsesquioxane powder (Note 4) | 0.5 |
| 13. Preservative | appropriate amount |
| 14. Fragrance | appropriate amount |
| 15. Crosslinked dimethylpolysiloxane (Note 5) | 4.0 |
| 16. Glyceryl trioctanoate | 2.0 |
| 17. Squalane | 1.0 |

(Note 1) treated with AES-3083 manufactured by Shin-Etsu Chemical Co., Ltd.
(Note 2) treated with KF-9909 manufactured by Shin-Etsu Chemical Co., Ltd.
(Note 3) KSP-300 manufactured by Shin-Etsu Chemical Co., Ltd.
(Note 4) KMP-590 manufactured by Shin-Etsu Chemical Co., Ltd.
(Note 5) KSG-16 manufactured by Shin-Etsu Chemical Co., Ltd.

(Production Method)

A: Components 1 to 13 are mixed and homogeneously ground.

B: Components 15 to 17 are homogeneously mixed and added to the mixture A.

C: Component 14 is added to the mixture B and press-molded in a mold. In this manner, powdery foundations were obtained.

The obtained powdery foundations were smooth and lightly spread, satisfactorily fitted with excellent adhesiveness, and further, the foundations were less sticky and resistant to perspiration, prolonged the wear of makeup and had excellent sense of use and usability.

Formulation Example 5

Pressed Powder

Pressed powders were prepared using the rutile-type titanium dioxides obtained in Examples 1 to 3.

| (Component) | Weight (%) |
|---|---|
| 1. Talc | balance |
| 2. PMMA (7 μm) (Note 1) | 10.0 |
| 3. Sericite | 30.0 |
| 4. Scaly-shaped silica (Note 2) | 3.0 |
| 5. Powder according to any one of Examples 1 to 3 | 6.0 |
| 6. Preservative | appropriate amount |
| 7. Colorant | appropriate amount |
| 8. Octyl methoxycinnamate | 3.0 |
| 9. Squalane | 2.0 |
| 10. Preservative | appropriate amount |
| 11. Antioxidant | appropriate amount |
| 12. Fragrance | appropriate amount |

(Note 1) Matsumoto Microsphere M-100 (manufactured by Matsumoto Yushi-Seiyaku Co., Ltd)
(Note 2) Sunlovely C (manufactured by Dokai Chemical Industries Co., Ltd)

(Production Method)

A: Components 1 to 7 are mixed and ground.

B: The mixture A is transferred to a Henschel mixer and Components 8 to 12 are added to the mixer, stirred and mixed to obtain a homogenous state.

C: The mixture B is ground by an atomizer and press-molded in an aluminum plate. In this manner, pressed powders were obtained.

It was confirmed that the obtained pressed powders are excellent in spreadability and smoothness during application and further provide a natural finish after application.

Formulation Example 6

2WAY Cake Foundation

2WAY cake foundations were prepared using the rutile-type titanium dioxides obtained in Examples 1 to 3.

| (Component) | Weight (%) |
|---|---|
| 1. Methicone-treated talc | balance |
| 2. Powder according to any one of Examples 1 to 3 | 10.0 |
| 3. Methicone-treated mica | 20.0 |
| 4. Methicone-treated sericite | 36.0 |
| 5. Nylon powder | 10.0 |
| 6. Methicone-treated yellow iron oxide | 1.0 |
| 7. Methicone-treated red iron oxide | 0.5 |
| 8. Methicone-treated black iron oxide | 0.1 |
| 9. Dimethylpolysiloxane 1000cs | 6.0 |
| 10. Isotridecyl isononanoate | 3.0 |
| 11. Squalane | 3.0 |
| 12. Preservative | 0.2 |
| 13. Antioxidant | 0.1 |

(Production Method)

A: Components 9 to 13 are dissolved by heating.

B: Components 1 to 8 are mixed by a Henschel mixer and the mixture A is added to this.

C: The mixture B is ground by an atomizer and press-molded in an aluminum plate. In this manner, 2WAY cake foundations were obtained.

It was confirmed that the obtained 2WAY cake foundations are excellent in spreadability and smoothness during application, further excellent in transparency after application and free of a powdery finish due to appropriate coverage, and provide a natural finish without concealing skin's natural beauty.

Formulation Example 7

Oily Cake Foundation

Oily cake foundations were prepared using the rutile-type titanium dioxides obtained in Examples 1 to 3.

| (Component) | Weight (%) |
|---|---|
| 1. Dimethicone-treated talc | 5.3 |
| 2. Powder according to anyone of Examples 1 to 3 | 15.0 |
| 3. Dimethicone-treated sericite | 28.2 |
| 4. Dimethicone-treated red iron oxide | 0.5 |
| 5. Dimethicone-treated yellow iron oxide | 1.8 |
| 6. Dimethicone-treated black iron oxide | 0.2 |
| 7. Candelilla wax | 1.0 |
| 8. Carnauba wax | 1.0 |
| 9. Ceresin | 1.5 |
| 10. Decamethylcyclopentasiloxane | 14.0 |
| 11. Isononyl isononanoate | balance |
| 12. Polyglyceryl diisostearate | 2.0 |
| 13. Dextrin palmitate | 1.0 |
| 14. Octyl methoxycinnamate | 3.0 |
| 15. Preservative | appropriate amount |
| 16. Fagrance | appropriate amount |

(Production Method)

A: Components 1 to 6 are mixed by a Henschel mixer and homogeneously ground.

B: Components 7 to 16 are dissolved by heating and the mixture A is added to this and homogeneously stirred.

C: After defoaming, a bulk is poured into a tray and gradually cooled to room temperature. In this manner, oily cake foundations were obtained.

It was confirmed that the obtained oily cake foundations are excellent in spreadability and smoothness during application, further excellent in transparency after application and free of a powdery finish due to appropriate coverage, and provide a natural finish without concealing skin's natural beauty.

Formulation Example 8

Stick Foundation

Stick foundations were prepared using the rutile-type titanium dioxides obtained in Examples 1 to 3.

| (Component) | Weight (%) |
|---|---|
| 1. Dimethylpolysiloxane | 18.0 |
| 2. Decamethylcyclopentasiloxane | 30.0 |
| 3. Octyl methoxycinnamate | 5.0 |
| 4. Diisostearyl malate | 4.0 |
| 5. Candelilla wax | 6.0 |
| 6. Hydrogenated jojoba ester | 4.0 |

-continued

| (Component) | Weight (%) |
|---|---|
| 7. Cetyldimethicone copolyl | 2.0 |
| 8. Sorbitan sesquiisostearate | 0.5 |
| 9. Antioxidant | appropriate amount |
| 10. Preservative | appropriate amount |
| 11. Fragrance | appropriate amount |
| 12. Methicone-treated colorant | 0.5 |
| 13. Powder according to any one of Examples 1 to 3 | 8.5 |
| 14. Methicone-treated talc | 6.0 |
| 15. Methicone-treated mica | 2.0 |
| 16. Methyl polymethacrylate | 2.0 |
| 17. Purified water | balance |
| 18. Sodium citrate | 0.3 |
| 19. 1,3-Butylene glycol | 3.0 |
| 20. Glycerin | 2.0 |
| 21. Preservative | appropriate amount |

(Production Method)

A: Components 12 to 16 are mixed by a Henschel mixer.

B: Components 1 to 11 are weighted in a container enough to contain a whole amount and dissolved by heating.

C: Components 17 to 21 are weighted in another container and dissolved by heating.

D: The mixture A is added to the mixture B and homogeneously dispersed and the mixture C was added and emulsified.

E: After deformation, a bulk is poured in a mold and gradually cooled to room temperature. In this manner, stick foundations were obtained.

It was confirmed that the obtained stick foundations are excellent in spreadability and smoothness during application, further excellent in transparency after application and free of a powdery finish due to appropriate coverage, and provide a natural finish without concealing skin's natural beauty.

Formulation Example 9

O/W Emulsion Type Foundation

O/W emulsion type foundations were prepared using the rutile-type titanium dioxides obtained in Examples 1 to 3.

| (Component) | Weight (%) |
|---|---|
| 1. Stearic acid | 0.4 |
| 2. Isostearic acid | 0.3 |
| 3. Cetyl 2-ethylhexanoate | 4.0 |
| 4. Liquid paraffin | 11.0 |
| 5. POE (10) stearyl ether | 2.0 |
| 6. Cetyl alcohol | 0.3 |
| 7. Preservative | 0.2 |
| 8. Talc | 15.0 |
| 9. Colorant | 4.0 |
| 10. Powder according to any one of Examples 1 to 3 | 3.0 |
| 11. Triethanolamine | 0.4 |
| 12. Propylene glycol | 5.0 |
| 13. Purified water | 54.1 |
| 14. Preservative | 0.2 |
| 15. Antioxidant | 0.1 |

(Production Method)

A: Components 1 to 7 are dissolved by heating at 85° C.

B: Components 8 to 10 are mixed and ground.

C: Components 11 to 15 are heated to 85° C., dissolved and mixed.

D: The mixture B is added to the mixture A and homogeneously dispersed. To the resultant mixture, the mixture C is gradually added. The mixture is emulsified and cooled to room temperature while stirring. Subsequently, an appropriate container is charged with the emulsion. In this manner, an O/W emulsion type foundations were obtained.

It was confirmed that the obtained O/W emulsion type foundations are excellent in spreadability and smoothness during application, further excellent in transparency after application and free of a powdery finish due to appropriate coverage, and provide a natural finish without concealing skin's natural beauty.

Formulation Example 10

Moisturizing O/W Cream

Moisturizing O/W creams were prepared using the rutile-type titanium dioxides obtained in Examples 1 to 3.

| (Component) | Weight (%) |
|---|---|
| 1. Crosslinked dimethylpolysiloxane (Note 1) | 8.0 |
| 2. Crosslinked dimethylpolysiloxane (Note 2) | 28.0 |
| 3. Decamethylcyclopentasiloxane | 10.0 |
| 4. Powder according to any one of Examples 1 to 3 | 5.0 |
| 5. Branched polyglycerin modified silicone (Note 3) | 0.3 |
| 6. Branched polyglycerin modified silicone (Note 4) | 0.6 |
| 7. (Acrylamide/acryloyldimethyltaurine Na) copolymer (Note 5) | 0.6 |
| 8. Dimethyltaurineammonium acrylate/VP copolymer (5% aqueous solution) (Note 6) | 12.0 |
| 9. Polyethylene glycol 400 | 1.0 |
| 10. Sodium lactate | 5.0 |
| 11. 1,3-Butylene glycol | 5.0 |
| 12. Purified water | 24.5 |

(Note 1) KSG-15 manufactured by Shin-Etsu Chemical Co., Ltd.
(Note 2) KSG-16 manufactured by Shin-Etsu Chemical Co., Ltd.
(Note 3) KF-6104 manufactured by Shin-Etsu Chemical Co., Ltd.
(Note 4) KF-6100 manufactured by Shin-Etsu Chemical Co., Ltd.
(Note 5) Simulgel 600 manufactured by SEPIC
(Note 6) Aristoflex AVC manufactured by Clariant (Production Method)

A: Components 3 to 5 are mixed and homogeneously dispersed.

B: Components 1 and 2 and the mixture A are mixed and homogeneously mixed.

C: Components 6 to 12 are homogeneously mixed.

D: The mixture B is gradually added to the mixture C with stirring to make an emulsion. In this manner, moisturizing O/W creams were obtained.

It was confirmed that the obtained moisturizing O/W creams are watery without stickiness or greasiness, lightly spread without squeaky feeling, have a fresh sense of use and pleasant cooling sensation; at the same time, the creams are moist and watery and extremely excellent in usability and stability without a change due to temperature and time.

Formulation Example 11

O/W Cream

O/W creams were prepared using the rutile-type titanium dioxides obtained in Examples 1 to 3.

| (Component) | Weight (%) |
|---|---|
| 1. Crosslinked dimethylpolysiloxane (Note 1) | 5.0 |
| 2. Powder according to any one of Examples 1 to 3 | 1.0 |

-continued

| (Component) | Weight (%) |
|---|---|
| 3. Glyceryl triisostearate | 8.0 |
| 4. Cetanol | 0.5 |
| 5. Stearic acid | 1.0 |
| 6. Glyceryl monostearate | 0.5 |
| 7. Sorbitan sesquioreate | 0.5 |
| 8. Polyoxyethylene sorbitan monooleate | 1.0 |
| 9. Triethanolamine | 0.5 |
| 10. Carbomer (1% aqueous solution) | 20.0 |
| 11. Locust bean gum (2% aqueous solution) | 5.0 |
| 12. 1,3-Butylene glycol | 7.0 |
| 13. Preservative | appropriate amount |
| 14. Fragrance | appropriate amount |
| 15. Purified water | 50.0 |

(Note 1) KSG-15 manufactured by Shin-Etsu Chemical Co., Ltd.

(Production Method)

A: Components 1 to 8 are heated, mixed and homogenized.

B: Components 9 to 13 and 15 are mixed and heated.

C: The mixture B is gradually added to the mixture A while stirring. The resultant mixture is emulsified and cooled and then, component 14 was added. In this manner, O/W creams were obtained.

It was confirmed that the obtained O/W creams are watery without stickiness or greasiness, have light spreadability and satisfactory adaptability with excellent adhesion, a fresh sense of use and pleasant cooling sensation; at the same time, the creams are moist and watery and excellent in usability and stability without a change due to temperature and time.

Formulation Example 12

Body Lotion

Body lotions were prepared using the rutile-type titanium dioxides obtained in Examples 1 to 3.

| (Component) | Weight (%) |
|---|---|
| 1. Alcohol | 17.0 |
| 2. 1,3-Butylene glycol | 3.0 |
| 3. Branched polyglycerin-modified silicone (Note 1) | 0.5 |
| 4. Glyceryl trioctanoate | 1.0 |
| 5. Powder according to any one of Examples 1 to 3 | 2.0 |
| 6. Hybrid silicone composite powder (Note 2) | 10.0 |
| 7. Dimethyltaurineammonium acrylate/VP polymer | 0.4 |
| 8. Xanthan gum (2% aqueous solution) | 6.0 |
| 9. Sodium chloride | 0.1 |
| 10. Purified water | 60.0 |

(Note 1) KF-6100 manufactured by Shin-Etsu Chemical Co., Ltd.
(Note 2) KSP-100 manufactured by Shin-Etsu Chemical Co., Ltd.

(Production Method)

A: Components 1 to 6 are homogeneously mixed.

B: Components 7 to 10 are homogeneously mixed.

C: The mixture A is gradually added to the mixture b while stirring. In this manner, body lotions were obtained.

It was confirmed that the obtained body lotions are watery without stickiness or greasiness, and have light spreadability and a moist, watery, fresh sense of use, pleasant cooling sensation, and extremely excellent usability and stability without a change due to temperature and time.

Formulation Example 13

Sunshine-Cut Cream

Sunshine-cut creams were prepared using the rutile-type titanium dioxides obtained in Examples 1 to 3.

| (Component) | Weight (%) |
|---|---|
| 1. Crosslinked polyether-modified silicone (Note 1) | 3.0 |
| 2. Crosslinked dimethylpolysiloxane (Note 2) | 2.0 |
| 3. Alkyl-modified branched polyether modified silicone (Note 3) | 1.0 |
| 4. Neopentylglycol dioctanate | 5.0 |
| 5. Decamethylcyclopentasiloxane | 17.5 |
| 6. Octyl methoxycinnamate | 6.0 |
| 7. Acrylic silicone resin dissolved product (Note 4) | 10.0 |
| 8. Caprylyl silane-treated fine particulate zinc oxide (Note 5) | 20.0 |
| 9. Powder according to any one of Examples 1 to 3 | 3.0 |
| 10. 1,3-Butylene glycol | 2.0 |
| 11. Sodium citrate | 0.2 |
| 12. Sodium chloride | 0.5 |
| 13. Fragrance | appropriate amount |
| 14. Purified water | 29.8 |

(Note 1) KSG-240 manufactured by Shin-Etsu Chemical Co., Ltd.
(Note 2) KSG-15 manufactured by Shin-Etsu Chemical Co., Ltd.
(Note 3) KF-6038 manufactured by Shin-Etsu Chemical Co., Ltd.
(Note 4) KP-575 manufactured by Shin-Etsu Chemical Co., Ltd.
(Note 5) AES-3083 manufactured by Shin-Etsu Chemical Co., (Production Method)

A: Component 7 is added to a part of component 5 and homogenized and components 8 and 9 are added and dispersed by a bead mill.

B: Components 1 to 4, the remainder of component 5 and component 6 are homogeneously mixed.

C: Components 10 to 12 and component 14 are mixed and homogenized.

D: The mixture C is added to the mixture B and emulsified, the mixture A and component 13 are added. In this manner, sunshine-cut creams were obtained.

It was confirmed that the obtained sunshine-cut creams can be applied on the skin uniformly since the surface coated with the cream is slightly distinguishable, have light spreadability without stickiness, satisfactory adaptability with excellent adhesiveness, and provide a fresh sense of use without greasiness; at the same time, the creams have satisfactory waterproofness, water repellency, perspiration fastness and extremely excellent makeup-lasting property, rarely come off and have excellent stability without a change due to temperature and time.

Formulation Example 14

Press-Type Brusher

Press-type brushers were prepared using the rutile-type titanium dioxides obtained in Examples 1 to 3.

| (Component) | Weight (%) |
|---|---|
| 1. Acrylic silicone resin-treated mica (Note 1) | 12.0 |
| 2. Silicone-treated talc (Note 2) | 72.1 |
| 3. Red pigment 202 | 0.3 |
| 4. Yellow iron oxide | 2.5 |
| 5. Black iron oxide | 0.3 |

-continued

| (Component) | Weight (%) |
|---|---|
| 6. Silicone-treated pigment-grade titanium dioxide (Note 2) | 0.5 |
| 7. Powder according to any one of Examples 1 to 3 | 0.3 |
| 8. Phenyl-modified hybrid silicone composite powder (Note 3) | 2.0 |
| 9. Dimethylpolysiloxane (6 $mm^2$/second (25° C.)) | 5.0 |
| 10. Vaseline | 2.0 |
| 11. Polyethylene wax | 3.0 |

(Note 1) Treated with KP-574 manufactured by Shin-Etsu Chemical Co., Ltd.
(Note 2) KF-9909 manufactured by Shin-Etsu Chemical Co., Ltd.
(Note 3) KSP-300 manufactured by Shin-Etsu Chemical Co., Ltd.

(Production Method)

A: Components 1 to 8 are homogeneously dispersed.

B: Components 9 to 11 are mixed by heating.

C: The mixture B is added to the mixture A and homogeneously mixed. The mixture is press-molded in a metal plate. In this manner, press-type brushers were obtained.

The obtained press-type brushers are lightly spread without greasiness, powdery or squeaky feeling and excellent in adhesiveness to skin, and provides a fresh sense of use; at the same time, the brushers are moist and satisfactory in waterproofness, water repellency, and perspiration fastness. The brushers rarely come off and have excellent stability without a change due to temperature and time.

Formulation Example 15

Loose Powder

Loose powders were prepared using the rutile-type titanium dioxides obtained in Examples 1 to 3.

| (Component) | Weight (%) |
|---|---|
| 1. Talc | balance |
| 2. Powder according to any one of Examples 1 to 3 | 1.0 |
| 3. Amihope LL | 3.0 |
| 4. PMMA (10 μm) (Note 1) | 8.0 |
| 5. Preservative | appropriate amount |
| 6. Colorant | appropriate amount |
| 7. Squalane | 1.0 |
| 8. Preservative | appropriate amount |
| 9. Antioxidant | appropriate amount |
| 10. Fragrance | appropriate amount |

(Note 1) Matsumoto Microsphere S-100 manufactured by Matsumoto Yushi-Seiyaku Co., Ltd.

(Production Method)

A: Components 1 to 7 are mixed and ground.

B: The mixture A is transferred to a Henschel mixer and components 8 to 10 are added, stirred and mixed so as to obtain a homogeneous state C: The mixture B is ground by an atomizer and charged. In this manner, loose powders were obtained.

It was confirmed that the obtained loose powders are excellent in spreadability and smoothness during application, excellent in transparency after application and free of a powdery finish due to appropriate coverage, and provide a natural finish without concealing skin's natural beauty.

Formulation Example 16

Eye Liner

Eye liners were prepared using the rutile-type titanium dioxides obtained in Examples 1 to 3.

| (Component) | Weight (%) |
|---|---|
| 1. Black iron oxide | 7.0 |
| 2. Powder according to any one of Examples 1 to 3 | 5.0 |
| 3. Vinyl acetate resin emulsion | 45.0 |
| 4. Concentrated glycerin | 6.0 |
| 5. POE (20)sorbitan laurate | 1.8 |
| 6. Carboxy methylcellulose (10% aqueous solution) | 18.0 |
| 7. Purified water | 14.9 |
| 8. Preservative | 0.1 |
| 9. Fragrance | 0.2 |

(Production Method)

A: Components 5 and 6 are added to component 7. To this, components 1 to 3 are added and treated by a colloid mill.

B: Components 4, 8 and 9 are mixed and the mixture A is added at 70° C. The resultant mixture is homogeneously dispersed, cooled and charged. In this manner, eye liners were obtained.

It was confirmed that the obtained eye liners are excellent in adhesiveness, makeup lasting property and color tone.

Example 17

Eyelash Liner

Eyelash liners were prepared using the rutile-type titanium dioxides obtained in Examples 1 to 3.

| (Component) | Weight (%) |
|---|---|
| 1. Water | 26.0 |
| 2. Polyvinylpyrrolidone | 2.0 |
| 3. Butylene glycol | 2.0 |
| 4. Cationized cellulose (1% aqueous solution) | 10.0 |
| 5. Bentonite | 0.5 |
| 6. Triethanolamine | 1.7 |
| 7. Talc | 2.7 |
| 8. Powder according to any one of Examples 1 to 3 | 1.0 |
| 9. Yellow iron oxide | 0.9 |
| 10. Red iron oxide | 0.9 |
| 11. Black iron oxide | 4.8 |
| 12. Carnauba wax | 5.5 |
| 13. Beeswax | 9.0 |
| 14. Stearic acid | 2.0 |
| 15. Self-emulsion type glyceryl stearate | 2.0 |
| 16. Propylene glycol stearate | 2.0 |
| 17. Hydrogenated polyisobutene | 2.0 |
| 18. Cyclomethicone | 4.0 |
| 19. Preservative | appropriate amount |
| 20. Antioxidant | appropriate amount |
| 21. Resin emulsion | 20.0 |

(Production Method)

A: Components 7 to 11 are stirred and mixed by a Henschel mixer.

B: The mixture A is added to Components 1 to 6 and homogeneously dispersed by a stirrer.

C: Components 12 to 20 are dissolved by heating in another container.

D: The mixture C is added to the mixture B. The resultant mixture is emulsified and cooled to 40° C. Component 21 is added and the mixture is cooled to room temperature. In this manner, eyelash liners were obtained.

It was confirmed that the obtained eyelash liners have appropriate gross and excellent adhesion to eyebrow, makeup lasting property and color tone.

Formulation Example 18

Cream Eye Shadow

Cream eye shadows were prepared using the rutile-type titanium dioxides obtained in Examples 1 to 3.

| (Component) | Weight (%) |
|---|---|
| 1. Acrylic silicone resin dissolved product (Note 1) | 10.0 |
| 2. Stearyl modified acrylic silicone resin (Note 2) | 2.0 |
| 3. Branched polyether-modified silicone (Note 3) | 1.5 |
| 4. Decamethylcyclopentasiloxane | 20.3 |
| 5. Isotridecyl isononanoate | 3.0 |
| 6. Dimethyldistearyl ammonium hectorite | 1.2 |
| 7. Acrylic silicone resin-treated pigment (Note 4) | 10.0 |
| 8. Powder according to any one of Examples 1 to 3 | 10.0 |
| 9. Spherical nylon | 3.0 |
| 10. Talc | 4.0 |
| 11. Ethanol | 5.0 |
| 12. Purified water | 30.0 |

(Note 1) KP-545 manufactured by Shin-Etsu Chemical Co., Ltd.
(Note 2) KP-561P manufactured by Shin-Etsu Chemical Co., Ltd.
(Note 3) KF-6028P manufactured by Shin-Etsu Chemical Co., Ltd.
(Note 4) Treated with KP-574 manufactured by Shin-Etsu Chemical Co., Ltd.

(Production Method)

A: Components 1 to 6 are mixed and components 7 to 10 are added, homogeneously mixed and dispersed.

B: Components 11 and 12 are mixed.

C: The mixture B is added to the mixture A and emulsified. In this manner, cream eye shadows were obtained.

It was confirmed that the obtained cream eye shadows are lightly spread and free of greasiness, powdery and squeaky feeling, and have excellent adhesiveness to skin and provide a fresh sense of use; at the same time, the eye shadows are moist and satisfactory in waterproofness, water repellency and perspiration fastness, and rarely come off and have excellent stability without a change due to temperature and time.

Formulation Example 19

Eye Shadow

Eye shadows were prepared using the rutile-type titanium dioxides obtained in Examples 1 to 3.

| (Component) | Weight (%) |
|---|---|
| 1. Methicone-treated talc | 36.5 |
| 2. Powder according to any one of Examples 1 to 3 | 9.0 |
| 3. Boron nitride | 9.0 |
| 4. Titanated Mica | 35.0 |
| 5. Dimethicone 1000cs | 5.0 |
| 6. Pigment red 202 | 0.5 |
| 7. Neopentyl glycol dioctanoate | 1.0 |
| 8. Squalane | 4.0 |
| 9. Preservative | appropriate amount |
| 10. Antioxidant | appropriate amount |

(Production Method)

A: Components 1 to 5 are mixed and ground.

B: The mixture A is transferred to a Henschel mixer, to which a mixture of components 6 to 10 separately prepared are added, stirred and mixed so as to obtain a homogenous state.

C: The mixture B is ground by an atomizer. This is press-molded in an aluminum plate. In this manner, eye shadows were obtained.

It was confirmed that the obtained eye shadows are excellent in makeup lasting property, adhesiveness, color tone and usability.

Formulation Example 20

Nail Enamel

Nail enamels were prepared using the rutile-type titanium dioxides obtained in Examples 1 to 3.

| (Component) | Weight (%) |
|---|---|
| 1. Nitro cellulose (½ second) | 10.0 |
| 2. Modified arkyd resin | 10.0 |
| 3. Acetyltributyl citrate | 5.0 |
| 4. Butyl acetate | 15.0 |
| 5. Ethyl acetate | 20.0 |
| 6. Ethanol | 5.0 |
| 7. Toluene | 35.0 |
| 8. Ultramarine blue | 0.5 |
| 9. Powder according to any one of Examples 1 to 3 | 0.1 |
| 10. Organic modified montmorillonite | 1.0 |

(Production Method)

A: Components 8 and 9 are dissolved in a part of Components 2 and 3 and sufficiently kneaded.

B: To the mixture A, the reminder of components 2 and 3, and components 1, 4 to 7 and 10 are added, mixed. A container is charged with the resultant mixture. In this manner, nail enamels were obtained.

It was confirmed that the obtained nail enamels are excellent in adhesiveness to nail, stability with time and color tone.

Formulation Example 21

Polyol-in-Solid Oil Emulsion Brusher

Polyol-in-solid oil emulsion brushers were prepared using the rutile-type titanium dioxides obtained in Examples 1 to 3.

| (Component) | Weight (%) |
|---|---|
| 1. Crosslinked polyglycerin modified silicone (Note 1) | 3.0 |
| 2. Crosslinked dimethylpolysiloxane (Note 2) | 5.0 |
| 3. Decamethylcyclopentasiloxane | 18.0 |
| 4. Dimethylpolysiloxane (6 $mm^2$/second (25° C.)) | 21.6 |
| 5. Cetyl isooctanoate | 5.0 |
| 6. Behenyl modified acrylic silicone resin (Note 2) | 3.0 |
| 7. Paraffin wax (melting point 80° C.) | 9.0 |
| 8. Dimethyldistearyl ammonium hectorite | 0.2 |
| 9. Powder according to any one of Examples 1 to 3 | 10.0 |
| 10. Acrylic silicone-treated blue 401 (Note 3) | 5.0 |
| 11. Acrylic silicone-treated black iron oxide (Note 3) | 0.2 |

-continued

| (Component) | Weight (%) |
|---|---|
| 12. Acrylic silicone-treated mica (Note 3) | 5.0 |
| 13. Preservative | appropriate amount |
| 14. Fragrance | appropriate amount |
| 15. 1,3-Butylene glycol | 15.0 |

(Note 1) KSG-710 manufactured by Shin-Etsu Chemical Co., Ltd.
(Note 2) KSG-15 manufactured by Shin-Etsu Chemical Co., Ltd.
(Note 3) KP-562P manufactured by Shin-Etsu Chemical Co., Ltd.

(Production Method)

A: Components 1 to 8 are heated to 80° C. and homogeneously mixed.

B: Components 9 to 12 are homogeneously mixed, added to the mixture A and homogeneously dispersed.

C: Components 13 and 15 are mixed and heated to 80° C.

D: The mixture C is added to the mixture B and emulsified, and component 14 is added. The resultant mixture is poured into a metal plate and cooled. In this manner, Polyol-in-solid oil emulsion brushers were obtained.

It was confirmed that the obtained polyol-in-solid oil emulsion brushers are non-aqueous products, which are lightly spread without stickiness or greasiness, have excellent adhesiveness without powdery feeling, and provide moisten skin after makeup and good stability with time.

Formulation Example 22

Brusher

Brushers were prepared using the rutile-type titanium dioxides obtained in Examples 1 to 3.

| (Component) | Weight (%) |
|---|---|
| 1. Talc | balance |
| 2. Sericite | 60.9 |
| 3. Fine particulate titanium dioxide | 3.0 |
| 4. Powder according to any one of Examples 1 to 3 | 2.0 |
| 5. Colorant | appropriate amount |
| 6. Octyl methoxycinnamate | 3.0 |
| 7. Octyl palmitate | 5.0 |
| 8. Preservative | appropriate amount |
| 9. Antioxidant | appropriate amount |

(Production Method)

A: Components 6 to 9 are dissolved by heating.

B: Components 1 to 5 are mixed by a Henschel mixer, to which the mixture A is added.

C: The mixture B is ground by an atomizer and molded in a medium plate. In this manner, brushers were obtained.

It was confirmed that the obtained brushers have excellent spreadability and smoothness during application and further provide a natural finish (the color of brushers on skin is indistinguishable from apparent color of products).

Formulation Example 23

Cream-Type Lip Stick

Cream-type lip sticks were prepared using the rutile-type titanium dioxides obtained in Examples 1 to 3.

| (Component) | Weight (%) |
|---|---|
| 1. Palmitic acid/dextrin ethylhexanoate (Note 1) | 9.0 |
| 2. Dipolyglyceryl triisostearate | 10.0 |
| 3. Glyceryl trioctanoate | 8.0 |
| 4. Alkyl-modified crosslinked dimethylpolysiloxane (Note 2) | 8.0 |
| 5. Alkyl-modified branched polyglycerin-modified silicone (Note 3) | 2.0 |
| 6. Decamethylcyclopentasiloxane | 40.0 |
| 7. 1,3-Butylene glycol | 5.0 |
| 8. Purified water | 18.0 |
| 9. Red pigment No. 201 | appropriate amount |
| 10. Red pigment No. 226 | appropriate amount |
| 11. Yellow pigment No. 4 | appropriate amount |
| 12. Powder according to any one of Examples 1 to 3 | appropriate amount |
| 13. Mica | appropriate amount |
| 14. Fragrance | appropriate amount |

(Note 1) Rheopearl TT, manufactured by Chiba Flour Milling Co., Ltd.
(Note 2) KSG-43 manufactured by Shin-Etsu Chemical Co., Ltd.
(Note 9) KF-6105 manufactured by Shin-Etsu Chemical Co., Ltd.

(Production Method)

A: Components 9 to 12 are added to a part of Component 2 and dispersed by a roller.

B: Component 1, the remainder of component 2 and components 3 to 6 are homogeneously mixed by heating.

C: The mixture A is added to the mixture B and homogeneously mixed.

D: Components 7 and 8 are mixed, warmed and then added to the mixture C and emulsified.

E: Components 13 and 14 are added to the mixture D. In this manner, cream-type lip sticks were obtained.

It was confirmed that the obtained cream-type lip sticks are lightly and easily spread on lips without stickiness or greasiness, retain moisture and give no feeling of dryness; at the same time, the lip sticks keep longer on lips without a powdery finish or bleeding and have good stability with time.

Formulation Example 24

Cleansing Foam

Cleansing foams were prepared using the rutile-type titanium dioxides obtained in Examples 1 to 3.

| (Component) | Weight (%) |
|---|---|
| 1. Lauric acid | 3.0 |
| 2. Myristic acid | 9.0 |
| 3. Palmitic acid | 8.0 |
| 4. Stearic acid | 10.0 |
| 5. Glycerin | 15.0 |
| 6. 1,3-Butylene glycol | 7.0 |
| 7. Glyceryl stearate | 1.5 |
| 8. Preservative | 0.2 |
| 9. Chelating agent | 0.1 |
| 10. Water | balance |
| 11. Potassium hydroxide | 6.0 |
| 12. Cocamidopropyl betaine | 3.3 |
| 13. Potassium cocoyl glycinate | 3.0 |
| 14. Glycosyl trehalose | 4.5 |
| 15. Powder according to any one of Examples 1 to 3 | 1.5 |

(Production Method)

A: Components 1 to 9 are mixed and dissolved by heating.

B: In another container, components 10 and 11 are weighed. The resultant mixture is added to the mixture A and saponified.

C: Components 12 to 15 are added to the mixture B and homogeneously stirred and mixed, and then cooled to room temperature. Subsequently, an appropriate container is charged with the mixture. In this manner, cleansing foams were obtained.

It was confirmed that the obtained cleansing foams have beautiful white apparent color and excellent foaming property and foams last long while keeping washing properties.

Formulation Example 25

Lip Stick

Lip sticks were prepared using the rutile-type titanium dioxides obtained in Examples 1 to 3.

| (Component) | Weight (%) |
|---|---|
| 1. Ceresin | 11.0 |
| 2. Carnauba wax | 1.0 |
| 3. Glyceryl 2-ethylhexanoate | 13.0 |
| 4. Mineral oil | 14.0 |
| 5. Hydrogenated polyisobutene | 20.0 |
| 6. Methylphenylpolysiloxane | 20.0 |
| 7. Octyldodecyl ricinoleate | 5.0 |
| 8. Red pigment No. 202 | 1.0 |
| 9. Powder according to any one of Examples 1 to 3 | 7.0 |
| 10. Titanated mica | 3.0 |
| 11. Antioxidant | appropriate amount |
| 12. Preservative | appropriate amount |

(Production Method)

A: Components 1 to 12 are mixed by heating and homogeneously stirred.

B: The mixture A is deformed and a bulk is poured into a mold, and quickly cooled. In this manner, lip sticks were obtained.

It was confirmed that the obtained lip sticks are excellent in gloss and have adhesion feeling and appropriate spreadability. If a general pigment-grade titanium dioxide is used, it is difficult to obtain a product providing the same color tone as apparent color of the product when applied to lips; however the lip sticks obtained in this example were confirmed to provide the same colors on lips as apparent colors of the lip stick products.

Formulation Example 26

Lip Gross

Lip grosses were prepared using the rutile-type titanium dioxides obtained in Examples 1 to 3.

| (Component) | Weight (%) |
|---|---|
| 1. Dextrin palmitate | 10.0 |
| 2. Diisostearyl malate | 44.0 |
| 3. Liquid paraffin | 42.6 |
| 4. Preservative | 0.1 |
| 5. Antioxidant | 0.1 |
| 6. Titanium mica | 0.1 |
| 7. Aluminum powder | 0.1 |
| 8. Powder according to any one of Examples 1 to 3 | 3.0 |

(Production Method)

A: Components 1 to 5 are heated to 85° C. and homogeneously dissolved.

B: To the mixture A, components 6 to 8 are added and homogeneously dispersed.

C: A container is charged with the resultant mixture at a high temperature and quickly cooled to room temperature. In this manner, lip grosses were obtained.

It was confirmed that the obtained lip grosses are excellent in adhesiveness and stability with time, and the colors on the lips are the same as apparent colors of the lip gross products.

What is claimed is:

1. A rutile-type titanium dioxide in a rectangular particulate form, comprising:

oriented and aggregated rutile-type titanium dioxide particles wherein each particle of the oriented and aggregated rutile-type titanium dioxide particles has a major axis diameter of from 30 to 200 nm and a minor axis diameter of from 3 to 10 nm, wherein the apparent average major axial length of the oriented and aggregated ruffle-type titanium dioxide particles is from 100 to 400 nm, wherein the apparent average minor axial length of the oriented and aggregated ruffle-type titanium dioxide particles is from 30 to 150 nm, wherein the apparent average axial ratio represented by the apparent average major axial length/the apparent average minor axial length is from 2 to 5, and wherein the specific surface area of the oriented and aggregated rutile-type titanium dioxide particles is from 10 to 100 $m^2/g$.

2. A rod shaped rutile-type titanium dioxide obtained by heating the rutile-type titanium dioxide in the rectangular particulate form according to claim 1 at a temperature of 300 to 700° C.

3. The rutile-type titanium dioxide according to claim 1, wherein a film formed from paste prepared by dispersing the rutile-type titanium dioxide in dimethicone has a value of ($T_{550}\times T_{280}/T_{360}$) of from 5.0 to 55.0 wherein a light transmissivity at a wavelength 550 nm, 360 nm, and 280 nm are represented by $T_{550}$, $T_{360}$, and $T_{280}$, respectively.

4. The rutile-type titanium dioxide according to claim 1, wherein surfaces of the oriented and aggregated rutile-type titanium dioxide particles are coated with a layer of an inorganic substance, an organic substance, or a combination thereof.

5. The rutile-type titanium dioxide according to claim 4, wherein the inorganic substance comprises at least one compound selected from the group consisting of aluminum, silicon, zinc, titanium, zirconium, iron, cerium, and tin.

6. The rutile-type titanium dioxide according to claim 4, wherein the organic substance comprises at least one compound selected from the group consisting of a silicone compound, a coupling agent, a fluorine compound, and a fatty acid.

7. A cosmetic, comprising:

the rutile-type titanium dioxide according to claim 1.

8. A method for producing the rutile-type titanium dioxide in the rectangular particulate form according to claim 1, the method comprising:

controlling pH of a solution comprising an acid-soluble titanium compound to from 1 to 3, subjecting the acid-soluble solution to a deflocculation treatment at a temperature of from 10 to 30° C. to generate a particle serving as a growth nucleus, adding hydrochloric acid to the acid-soluble solution comprising the growth nucleus, and performing a hydrolysis reaction at a temperature of 20 to 80° C. to form oriented and aggregated particles of rutile-type titanium dioxide in the rectangular particulate form.

9. A method for producing the rod-shaped rutile-type titanium dioxide according to claim 2, the method comprising:

controlling pH of a solution comprising an acid-soluble titanium compound to from 1 to 3, subjecting the acid-soluble solution to a deflocculation treatment at a temperature of 10 to 30° C. to generate a red-shaped particle serving as a growth nucleus, adding hydrochloric acid to the acid-soluble solution comprising the growth nucleus, performing a hydrolysis reaction at a temperature of 20 to 80° C. to form oriented and aggregated particles of the rutile-type titanium dioxide in the rectangular particulate form, and heating the oriented and aggregated particles of the rutile-type titanium dioxide in the rectangular particulate at a temperature of 300 to 700° C. to form the rod-shaped rutile-type titanium dioxide.

* * * * *